United States Patent
Wang et al.

(10) Patent No.: US 9,943,243 B2
(45) Date of Patent: Apr. 17, 2018

(54) CARD TYPE ELECTROCARDIO MEASURING DEVICE

(71) Applicant: BEIJING FINLTOP BIOLOGICAL TECHNOLOGY CO., LTD., Beijing (CN)

(72) Inventors: Yaoxing Wang, Beijing (CN); Shaozhi Liu, Beijing (CN)

(73) Assignee: BEIJING FINLTOP BIOLOGICAL TECHNOLOGY CO., LTD., Beijing (CN)

(*) Notice: Subject to any disclaimer, the term of this patent is extended or adjusted under 35 U.S.C. 154(b) by 795 days.

(21) Appl. No.: 14/530,641

(22) Filed: Oct. 31, 2014

(65) Prior Publication Data

US 2015/0051472 A1 Feb. 19, 2015

Related U.S. Application Data

(63) Continuation of application No. PCT/CN2014/072013, filed on Feb. 13, 2014.

(30) Foreign Application Priority Data

Jun. 7, 2013 (CN) .......................... 2013 1 0226564
Jun. 7, 2013 (CN) ..................... 2013 2 0329553 U (51) Int. Cl.
*A61B 5/0404* (2006.01)
*A61B 5/04* (2006.01)
(Continued)

(52) U.S. Cl.
CPC ............ *A61B 5/0404* (2013.01); *A61B 5/044* (2013.01); *A61B 5/04017* (2013.01);
(Continued)

(58) Field of Classification Search
CPC . A61B 5/0404; A61B 5/7455; A61B 5/04085; A61B 5/044; A61B 5/04017;
(Continued)

(56) References Cited

U.S. PATENT DOCUMENTS 4,596,256 A 6/1986 Ascher et al. ................ 128/710
4,755,035 A * 7/1988 Kopish ............... G02B 6/0081
349/58

(Continued)

FOREIGN PATENT DOCUMENTS

CN 86102464 A 10/1987
CN 2413642 Y 1/2001
(Continued)

OTHER PUBLICATIONS

Chinese International Search Report of corresponding International PCT Application No. PCT/CN2014/072013, dated May 21, 2014.
(Continued)

*Primary Examiner* — Lee S Cohen
*Assistant Examiner* — Eunhwa Kim
(74) *Attorney, Agent, or Firm* — J.C. Patents (57) ABSTRACT

Disclosed is a card type electrocardio measuring device, including: a circuit board (101), a main body bracket (102) and a back encapsulation; the circuit board (101) is arranged on the front of the main body bracket (102); the back encapsulation is arranged on the back of the main body bracket (102); the main body bracket (102) has a hollow shape, and electronic components on the circuit board (101) are respectively accommodated fitly between the back of the circuit board (101) and the back encapsulation, in a way of penetrating a hollow portion of the main body bracket (102).

18 Claims, 7 Drawing Sheets

(51) Int. Cl.
*A61B 5/0402* (2006.01)
*A61B 5/0408* (2006.01)
*A61B 5/044* (2006.01)
*A61B 5/0428* (2006.01)
*A61B 5/00* (2006.01)

(52) U.S. Cl.
CPC ...... *A61B 5/04021* (2013.01); *A61B 5/04085* (2013.01); *A61B 5/7455* (2013.01); *A61B 5/04288* (2013.01); *A61B 5/7203* (2013.01)

(58) Field of Classification Search
CPC ............ A61B 5/04021; A61B 5/04288; A61B 5/7203
See application file for complete search history.

(56) References Cited

U.S. PATENT DOCUMENTS

| | | | | |
|---|---|---|---|---|
| 5,289,824 A | * | 3/1994 | Mills | A61B 5/0404 128/904 |
| 5,834,714 A | * | 11/1998 | Berger | H01H 13/702 200/1 B |
| 2004/0260190 A1 | * | 12/2004 | Tanabe | A61B 5/0404 600/509 |
| 2005/0154324 A1 | * | 7/2005 | Lin | A61B 5/0404 600/509 |
| 2006/0217620 A1 | * | 9/2006 | Bojovic | A61B 5/0006 600/509 |
| 2008/0234592 A1 | * | 9/2008 | Lim | A61B 5/0006 600/509 |
| 2010/0042008 A1 | | 2/2010 | Amitai | 600/509 |

FOREIGN PATENT DOCUMENTS

| | | |
|---|---|---|
| CN | 1586393 A | 3/2005 |
| CN | 201438963 U | 4/2010 |
| CN | 101879090 A | 11/2010 |
| CN | 103330558 A | 10/2013 |
| CN | 203341731 U | 12/2013 |
| CN | 103330558 B | 6/2015 |
| WO | WO2011094399 A2 | 8/2011 |
| WO | WO2013054477 A1 | 4/2013 |

OTHER PUBLICATIONS

Chinese First Examination Report of corresponding China Application No. 201310226564.2, dated Sep. 3, 2014.

* cited by examiner

FIG. 8

CARD TYPE ELECTROCARDIO MEASURING DEVICE

CROSS REFERENCE TO RELATED APPLICATIONS

This application is a continuation of International Application No. PCT/CN2014/072013, filed on Feb. 13, 2014, which claims priority to China Patent Application No. 201310226564.2, 201320329553.2, both filed with the Chinese Patent Office, on Jun. 7, 2013, entitled "CARD TYPE ELECTROCARDIO MEASURING DEVICE", both of which are hereby incorporated herein by reference in their entireties.

TECHNICAL FIELD

The present invention relates to the field of medical devices, and in particular to a portable card type electrocardio measuring device capable of timely measuring electrocardio waveforms.

BACKGROUND

Nowadays, people are becoming increasingly concerned about their health. In daily life, the patient is always subconsciously aware of his heart going wrong when going through the following experience: having discomforts, such as palpitations, fatigue, shortness of breath, or a sense of breathing difficulty for daily or physical activities; sudden retrosternal pain or chest tightness when tired or stressed; too fast, too slow, deficit or irregular pulse; sudden awakening during sleeping or nightmare, having palpitations, chest tightness, shortness of breath, it is necessary to sit up for a moment before upturn; having a sense of breathing difficulty, chest tightness or chest pain in a sexual experience; having a sense of palpitations, chest tightness or chest pain after a generous meal, or when it is cold, or when smoking or watching an intensive movie or TV; having chest tightness, shortness of breath, or a sense of breathing difficulty in a public place; easier to feel palpitations or shortness of breath than before or than others when going upstairs; having a burst of sudden palpitations, dizziness, sudden blackouts, a sense of falling; having a sense of abnormal heart beat sound at rest, or quiver feeling when a palm touches a heart position of the anterior chest wall; indeed, the occurrence of such phenomena may be early symptom of inducing cardiac disease.

Since the above phenomena is often a contingent event for most patients, they cannot obtain timely medical treatment during the attacks, and after the event, the only thing they could do is to state their feeling at that moment to a doctor, and there was nothing unusual in a conventional electrocardio waveform measurement; even if a Holter (dynamic electrocardio measuring meter) is used to perform continuous monitoring and measurement for 24 hours, it is also difficult to capture effective diagnostic evidences according to one or several electrocardio waveforms, but the patient may occasionally have obvious self-conscious symptoms.

Compared to a conventional heavy medical electrocardio monitor, the commercially available portable electrocardio measuring device at present is more suitable for domestic use; however, since its internal structure is complex, assembling of relevant major structures and circuit boards is cumbersome, and the volume of the product is somewhat heavy, it is not as convenient to carry as electronic products, such as a mobile phone or a PDA. In the outdoor or a public place, when a patient suffers from a self-conscious symptom, such as palpitations or ecphysesis, which needs to perform electrocardio measurement, the existing portable electrocardio measuring device cannot offer service of electrocardio waveform measurement for the patient at any time due to a restriction of the product volume and inconvenience to carry.

SUMMARY

The present invention is directed to solving at least one of those problems in the prior art to some extent. Accordingly, one object of the present invention is to provide a card type electrocardio measuring device, for a purpose of enabling the device to be thinner, smaller and more convenient to carry.

In order to achieve the above object, the present invention provides a card type electrocardio measuring device, including a main body bracket, with a hollow shape; a back encapsulation, arranged on the back of the main body bracket; and a circuit board, arranged on the front of the main body bracket, where electronic components on the circuit board are respectively accommodated fitly between the back of the circuit board and the back encapsulation, in a way of penetrating a hollow portion of the main body bracket.

In some embodiments of the present invention, the electronic components are all arranged on the back of the circuit board, and the front of the circuit board and the front frame of the main body bracket are in the same horizontal plane.

In some embodiments of the present invention, the back encapsulation includes a back bracket and the four back touch electrodes, and the four back touch electrodes are arranged around the back bracket.

In some embodiments of the present invention, outer edges of the back touch electrodes and vertex angles are shaped to be arc chamfers.

In some embodiments of the present invention, the back bracket comprises a sheet-shaped body and a plurality of projections, and the plurality of projections are respectively perpendicular to the sheet-shaped body; the main body bracket is correspondingly provided with blind holes for engaging the projections; the back bracket is snapped into the back of the main body bracket, and the plurality of the projections are respectively embedded into the blind holes to fixedly connect the back bracket and the main body bracket.

In some embodiments of the present invention, the back bracket is made of metallic materials, and the back bracket and the main body bracket are integrally molded.

In some embodiments of the present invention, the back touch electrode includes a horizontal engaging portion and a vertical welding portion, and the main body bracket is correspondingly provided with through-holes for engaging the vertical welding portion; the horizontal engaging portion is embedded into both edges of the back bracket's exterior corner, and the vertical welding portion passes through the through-hole to weld with the circuit board.

In some embodiments of the present invention, the top of the portion where the vertical welding portion passes through the through-hole, the vertical welding portion and the front frame of the main body bracket are in the same horizontal plane.

In some embodiments of the present invention, the four back touch electrodes comprise a back left feedback touch electrode, a back right feedback touch electrode, a back positive touch electrode and a back negative touch electrode; the circuit board comprises an electrode circuit and a filter circuit, where the electrode circuit comprises a positive electrode, a negative electrode and a feedback electrode, which are respectively connected with the filter circuit; the positive electrode and the negative electrode are used to introduce body potential change of a subject to the filter circuit; the feedback electrode is used to help the positive electrode and the negative electrode to filter out a noise signal into a front end of the filter circuit; the back left feedback touch electrode and the back right feedback touch electrode are respectively arranged at the left lower corner and the right lower corner of the back of the main body bracket and connected with the feedback electrode; the back positive touch electrode and the back negative touch electrode are respectively arranged at the left upper corner and the right upper corner of the back of the main body bracket and connected with the positive electrode and the negative electrode.

In some embodiments of the present invention, further including: a strip-shaped battery, where the circuit board is provided with a battery hollow portion for accommodating fitly the strip-shaped battery; the strip-shaped battery is arranged within the battery hollow portion along its long edge, with one side being against the back encapsulation, and the other side and the front of the circuit board being in the same horizontal plane.

In some embodiments of the present invention, further including: a head-on positive touch electrode and a head-on negative touch electrode, arranged on the front of the circuit board and at the two sides of the battery hollow portion, and respectively connected with the positive electrode and the negative electrode.

In some embodiments of the present invention, further including: a buzzer and an LCD, where the main body bracket is provided with a buzzer slot for accommodating fitly the buzzer and an LCD slot for engaging the LCD, the LCD slot is located above the buzzer slot; the circuit board is provided with an LCD hollow portion for accommodating fitly the LCD; the buzzer is provided within the buzzer slot; and the LCD engages the LCD slot via the LCD hollow portion and is supported by the buzzer slot.

In some embodiments of the present invention, an LCD panel of the LCD engaged the LCD slot and the front of the circuit board are in the same horizontal plane.

In some embodiments of the present invention, the buzzer slot is of a split structure, and a gap of the split structure is for accommodating fitly a line connecting the buzzer and the circuit board.

In some embodiments of the present invention, further including: a strong seal for sealing the front of the circuit board, on which it is provided with an electrode through-hole for revealing the head-on positive touch electrode and the head-on negative touch electrode.

In some embodiments of the present invention, further including: a strong seal for sealing the front of the circuit board, on which it is provided with a window for transparently sealing the LCD.

In some embodiments of the present invention, the circuit board is printed with a first break-point annular switch for switching a power source and a second break-point annular switch for activating measurement, both the first break-point annular switch and the second break-point annular switch comprise an annular electrode and a circular electrode, which are arranged concentrically and insulated from each other through a circular groove.

In some embodiments of the present invention, further including: a strong seal, for sealing the front of the circuit board, which is provided with elastic switches respectively corresponding to the first break-point annular switch and the second break-point annular switch for turning on the first break-point annular switch and the second break-point annular switch.

In some embodiments of the present invention, the elastic switch is a raised elastic tongue, wherein the annular electrode and the circular electrode are electrically connected by pressing the elastic tongue to a flatten state.

Due to the adoption of relevant technical solutions that: the circuit board is arranged on the front of the main body bracket, the back encapsulation is arranged on the back of the main body bracket, and electronic components on the circuit board are respectively accommodated fitly between the back of the circuit board and the back encapsulation, in a way of penetrating a hollow portion of the main body bracket, the device is thinner as a whole, and also has features of simple structure, convenient production assembly, compact structure, small size and portability, and thus can offer service of electrocardio waveform measurement for a patient at any time, when the patient suffers from a self-conscious symptom, such as palpitations or ecphysesis.

Additional aspects and advantages of the present invention will be set forth in part in the description that follows and in part will be obvious from the description, or may be learned by practice of the present invention.

BRIEF DESCRIPTION OF DRAWINGS

These and/or additional aspects and/or advantages of the present invention will become more apparent and more readily appreciated from the following description of the embodiments, taken in conjunction with the accompanying drawings, in which.

DESCRIPTION OF EMBODIMENTS

A detailed description of the embodiments of the present invention is provided herein below, by way of example only, with reference to the accompanying drawings, in which identical or similar reference numerals refer to the identical or functionally similar elements throughout the description. The following description of the embodiments with reference to the accompanying drawings is illustrative, which is only intended to illustrate the present invention but is not to be construed as limiting the present invention.

Embodiment 1

Figure 1:
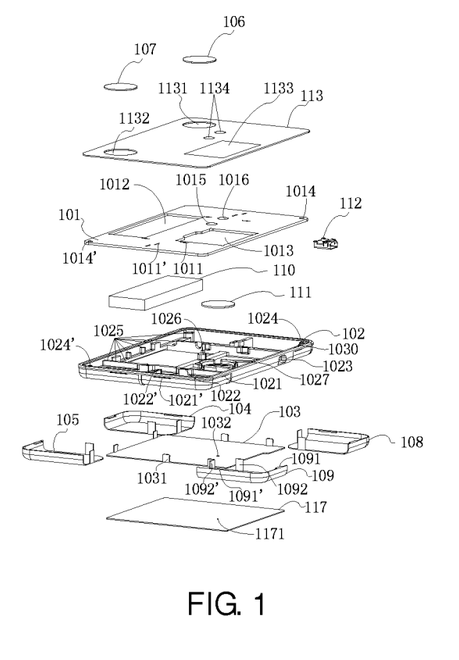
FIG. 1 is an exploded schematic diagram of an assembly structure of a card type electrocardio measuring device according to the present invention.
Figure 2:
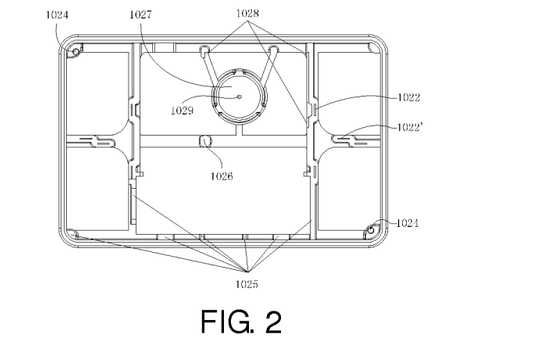
FIG. 2 is a structural schematic diagram of a main body bracket of a card type electrocardio measuring device according to the present invention.

FIG. 1 is an exploded schematic diagram of an assembly structure of a card type electrocardio measuring device according to the present invention. FIG. 2 is a structural schematic diagram of a main body bracket of a card type electrocardio measuring device according to the present invention. With reference to FIG. 1 and FIG. 2, the card type electrocardio measuring device in this embodiment includes a circuit board 101, a main body bracket 102 and a back encapsulation. The back encapsulation includes a back bracket 103 and four back touch electrodes, in particular, the back bracket 103 includes a sheet-shaped body and six projections 1031, and the six projections 1031 are respectively perpendicular to the sheet-shaped body and uniformly distributed on the edges of the sheet-shaped body, blind holes for engaging the projections 1031 are arranged on the main body bracket 102 corresponding to the six projections 1031, and the back bracket 103 and the main body bracket 102 are fixedly connected by snapping the back bracket 103 into the back of the main body bracket 102, wherein the projections 1031 are respectively embedded into the blind holes. Of course, the number of the projections 1031 can be adjusted based on the actual situations, as long as the projections 1031 are respectively perpendicular to the sheet-shaped body and uniformly distributed on the edges of the sheet-shaped body, and blind holes for engaging the projections 1031 are arranged on the main body bracket 102 at a place corresponding to the projections 1031. Further, the back bracket 103 is preferably made of metallic materials, and is integrally molded with the back bracket 103 to fixedly connect the back bracket 103 and the main body bracket 102. In practice, if the back bracket 103 is a separate plastic member, the back bracket 103 connects with the main body bracket 102 in an inserting manner, which is difficult to guarantee the overall structural strength of the back bracket 103 and the main body bracket 102; if both the back bracket 103 and the main body bracket 102 are integrally molded with plastic materials, under the existing injection molding process condition, the injection molding thickness of the overall area have to be more than 1 mm in order to guarantee the overall structural strength, which virtually increases the overall thickness of the card type electrocardio measuring device; however, when the back bracket 103 is preferably made of metallic materials, and the structure of the main body bracket 102 is molded on the structural basis of the back bracket 103, the process is simpler, the overall structural strength of the back bracket 103 and the main body bracket 102 is higher, and the thickness of the back bracket 103 can maintain 0.3 mm, which can greatly reduce the overall thickness of the card type electrocardio measuring device.

Further, the four back touch electrodes specifically include a back left feedback touch electrode 104, a back right feedback touch electrode 105, a back positive touch electrode 108 and a back negative touch electrode 109, these back touch electrodes surround the back bracket 103 and are respectively arranged at the left upper corner and the right upper corner, the left lower corner and the right lower corner of the main body bracket 102, and due to an isolation structure of the back frame of the main body bracket 102, these back touch electrodes are not in contact with each other and are all not in contact with the back bracket 103; where the back left feedback touch electrode 104 and the back negative touch electrode 109 are homotypic, the back right feedback touch electrode 105 and the back positive touch electrode 108 are homotypic, the back negative touch electrode 109, the back right feedback touch electrode 105 and the back positive touch electrode 108 are mirror symmetric; the four back touch electrodes will be described by taking the structure of the back negative touch electrode 109 and the connecting mode with the main body bracket 102 as an example, in particular, the back negative touch electrode 109 includes horizontal engaging portions 1091, 1091' and vertical welding portions 1092, 1092', both edges of the back right upper exterior corner of the main body bracket 102 are respectively arranged with engaged holes 1021, 1021' for engaging the horizontal engaging portions 1091, 1091', right upper interior corner of the main body bracket 102 are respectively arranged with through-holes 1022, 1022' for engaging the vertical welding portions 1092, 1092', and the back negative touch electrode 109 and the main body bracket 102 are fixedly connected together by embedding the horizontal engaging portions 1091, 1091' respectively into the engaged holes 1021, 1021' with the vertical welding portions 1092, 1092' passing through the through-holes 1022, 1022', as shown in FIG. 1, welding holes 1011, 1011', which places are correspond to through-holes 1022, 1022', are arranged on the circuit board 101, tops of the vertical welding portions 1092, 1092' are embedded into the welding holes 1011, 1011' respectively while vertical welding portions 1092, 1092' passes through the through-holes 1022, 1022', in addition, by means of spot welding, the right upper corner of the circuit board 101, which is originally overlapped on the main body bracket 102 before assembling, can fixedly connect with the right upper corner of the main body bracket 102 through the back negative touch electrode 109. Likewise, the connecting mode of other corner and the main body bracket 102 is the same as the connecting mode of the right upper corner with the main body bracket 102, which will not be described herein again.

Further, during measurement of the electrocardio waveforms, the outer edges and vertex angles of the back touch electrodes are all shaped to be arc chamfers, so as to improve the comfort degree of the measuring postures.

It should be emphasized that the circuit board 101 can be set up in the main body bracket 102 via various shaped steps 1025 in the same horizontal plane within the main body bracket 102, and can be arranged in alignment with circular holes 1014, 1014' via cylinders 1024, 1024', before assembling the card type electrocardio measuring device, so as to position the circuit board 101 on the edges of the main body bracket 102. Further, since the dimension of the circuit board 101 is only about 82 mm*52 mm, and the sheet material is slightly thin (only 0.8 mm), in view of the strength of the circuit board 101, the main body bracket 102 is correspondingly provided with a central support column 1026, the top of which and the step 1025 are in the same horizontal plane, therefore, the central support column 1026 can be used to support the middle of the circuit board 101, so as to provide more protection to the circuit board 101.

Further, the top of central support column 1026 also can be slightly above the step 1025, and the back of the circuit board 101 is provided with a blind hole groove (not shown in FIG. 1) for matching with the central support column 1026, so as to rest against the top of the central support column 1026 and then position the circuit board 101 in the center of the main body bracket 102, and the circuit board 101 can be attached to the main body bracket 102 more accurately, so as to provide more protection to the circuit board 101 and improve reliability of the overall strength of the device.

In order to guarantee design requirements for the overall thickness of the card type electrocardio measuring device in this embodiment, on the one hand, all the electronic components on the circuit board 101 should be designed on the back, as shown in FIG. 1 and FIG. 2, since the main body bracket 102 has a hollow shape, these electronic components can make full use of the space, and are accommodated fitly between the back of the circuit board 101 and the back encapsulation, in a way of penetrating a hollow portion of the main body bracket 102, here, the "being accommodated fitly" means that, the electronic components welded on the circuit board 101 is in clearance fit with the back encapsulation, that is, the height of the electronic components welded on the circuit board 101 makes full use of a distance between the back of the circuit board 101 and the back encapsulation; on the other hand, the front of the circuit board 101 is provided with a head-on positive touch electrode 106 and a head-on negative touch electrode 107 suitable for being pressed by a thumb, besides, the front of the circuit board 101 is not provided with electronic components, and it should be emphasized that the head-on positive touch electrode 106 and the head-on negative touch electrode 107 herein are not electronic components but sheet metals for increasing touch hand feeling and touch area.

Further, the card type electrocardio measuring device also includes a strong seal 113 for sealing the front of the circuit board 101, the strong seal 113 is made of plastic materials, with the back pasted with strong viscose, the strong seal 113 is reserved with electrode through-holes 1131, 1132 for revealing the head-on positive touch electrode 106 and the head-on negative touch electrode 107, in order to get a better overall encapsulating effect, the strong seal 113 has the same thickness with the head-on positive touch electrode 106 and the head-on negative touch electrode 107. In order to further make the strong seal 113 provided on the front of the circuit board 101 more fit, durable and elegance, on the one hand, the front of the circuit board 101 and the front frame of the main body bracket 102 should be in the same horizontal plane after the circuit board 101 is arranged in the main body bracket 102; on the other hand, the front of the circuit board 101 should be flat, that is why the front of the circuit board 101 is not provided with electronic components, besides, in order to keep the front of the circuit board 101 flat, the card type electrocardio measuring device further includes a strip-shaped battery 110, the circuit board 101 is provided with a battery hollow portion 1012 for accommodating the strip-shaped battery 110 fitly, the electrode through-holes 1131, 1132 for revealing the head-on positive touch electrode 106 and the head-on negative touch electrode 107 are respectively located at both sides of the battery hollow portion 1012, and the strip-shaped battery 110 is arranged within the battery hollow portion 1012 along its long edge, with one side being against the back encapsulation, and the other side and the front of the circuit board 101 being in the same horizontal plane; besides, in order to keep the front of the circuit board 101 flat, the card type electrocardio measuring device further includes a buzzer 111 and an LCD (not shown in both FIG. 1 and FIG. 2), the main body bracket 102 is provided with a buzzer slot 1027 for accommodating the buzzer 111 fitly, and an LCD slot 1028 for engaging the LCD, the LCD slot 1028 is located above the buzzer slot 1027, the circuit board 101 is correspondingly provided with an LCD hollow portion 1013 for accommodating the LCD fitly, in a shaped card type electrocardio measuring device, the buzzer 111 is provided within the buzzer slot 1027, and the LCD is engaged with the LCD slot 1028 via an LCD hollow portion 1013 and supported by the buzzer slot 1027, the LCD panel of the LCD for engaging the LCD slot 1028 and the front surface of the circuit board 101 are in the same horizontal plane, further, a strong seal 113 is provided with a window 1133 for transparently sealing the LCD for watching the LCD; besides, in order to keep the front of the circuit board 101 flat, taking the structure of the back negative touch electrode 109 as an example, tops of the vertical welding portions 1092, 1092' revealing the through-holes 1022, 1022' have heights of less than 0.8 mm, that is, not more than the thickness of the circuit board 101, or the top of the portion where the vertical welding portion 1092, 1092' revealing the through-holes 1022, 1022' and the front frame of the main body bracket 102 are in the same horizontal plane, likewise, vertical welding portions of other back touch electrodes also have the same requirements.

Further, the buzzer slot 1027 is of a split structure, it can be understood that a gap of the split structure is for accommodating fitly a line connecting the buzzer 111 and the circuit board 101, which can make full use of the space and thus prevent a trace of a jump wire from increasing the overall thickness of the card type electrocardio measuring device. Furthermore, a main buzzer hole 1029 is arranged in the center of the buzzer slot 1027, correspondingly, a supplementary buzzer hole 1171 is arranged on a seal 117 for sealing the back bracket 103, and the main buzzer hole 1029 matches with the supplementary buzzer hole 1171 to conduct sound produced by the buzzer 111. Furthermore, the seal 117 can be used for indicating a nameplate and relevant required information and parameters of the card type electrocardio measuring device.

Figure 3:
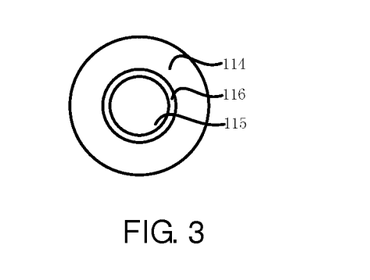
FIG. 3 is a structural schematic diagram of a break-point annular switch of a card type electrocardio measuring device according to the present invention.

Further, in order to guarantee design requirements for the overall thickness of the card type electrocardio measuring device in this embodiment, on the one hand, a charging interface 112 included in the card type electrocardio measuring device in this embodiment makes full use of the thickness of the main body bracket 102, connects to the circuit board 101, and is arranged in a charging interface through-hole 1023 provided at the side of the main body bracket 102; on the other hand, a switch system of the card type electrocardio measuring device in this embodiment is provided on the front of this device, since it is required that the front of the circuit board 101 in this embodiment is not provided with electronic components and the front of the circuit board 101 should be flat, the circuit board is printed with (by a copper etching technique) a first break-point annular switch 1015 for switching a power source, and a second break-point annular switch 1016 for enabling a test measurement, as shown in FIG. 3, which is a structural schematic diagram of a break-point annular switch of a card type electrocardio measuring device according to the present invention, the first break-point annular switch 1015 or the second break-point annular switch 1016 specifically includes an annular electrode 114 and a circular electrode 115, the circular electrode 115 is arranged in the annular electrode 114, and is arranged concentrically and insulated from each other through a circular groove 116, further, the strong seal 113 is provided with elastic switches 1134 respectively corresponding to the first break-point annular switch 1015 and the second break-point annular switch 1016 for turning on the first break-point annular switch 1015 and the second break-point annular switch 1016, in particular, the elastic switch 1134 is a raised elastic tongue, the annular electrode 114 and the circular electrode 115 are electrically connected by pressing the elastic tongue to a flatten state.

The specific structure of the card type electrocardio measuring device in this embodiment is described in detail with reference to FIG. 1 to FIG. 3, due to the adoption of relevant technical solutions that: the circuit board is arranged on the front of the main body bracket, the back encapsulation is arranged on the back of the main body bracket, and electronic components on the circuit board are respectively accommodated fitly between the back of the circuit board and the back encapsulation, in a way of penetrating a hollow portion of the main body bracket, the device is thinner as a whole; besides, the circuit board is designed to be about 82 mm*52 mm, which makes the device being small in size as a whole; furthermore, the strong seal is provided on the front of the flat circuit board more fit, durable and elegant, which not only makes the overall device simple in structure, convenient in production assembly, but also compact in structure and portability, and thus can offer service of electrocardio waveform measurement for a patient at any time, when the patient suffers from a self-conscious symptom, such as palpitations or ecphysesis.

Embodiment 2

Figure 4:
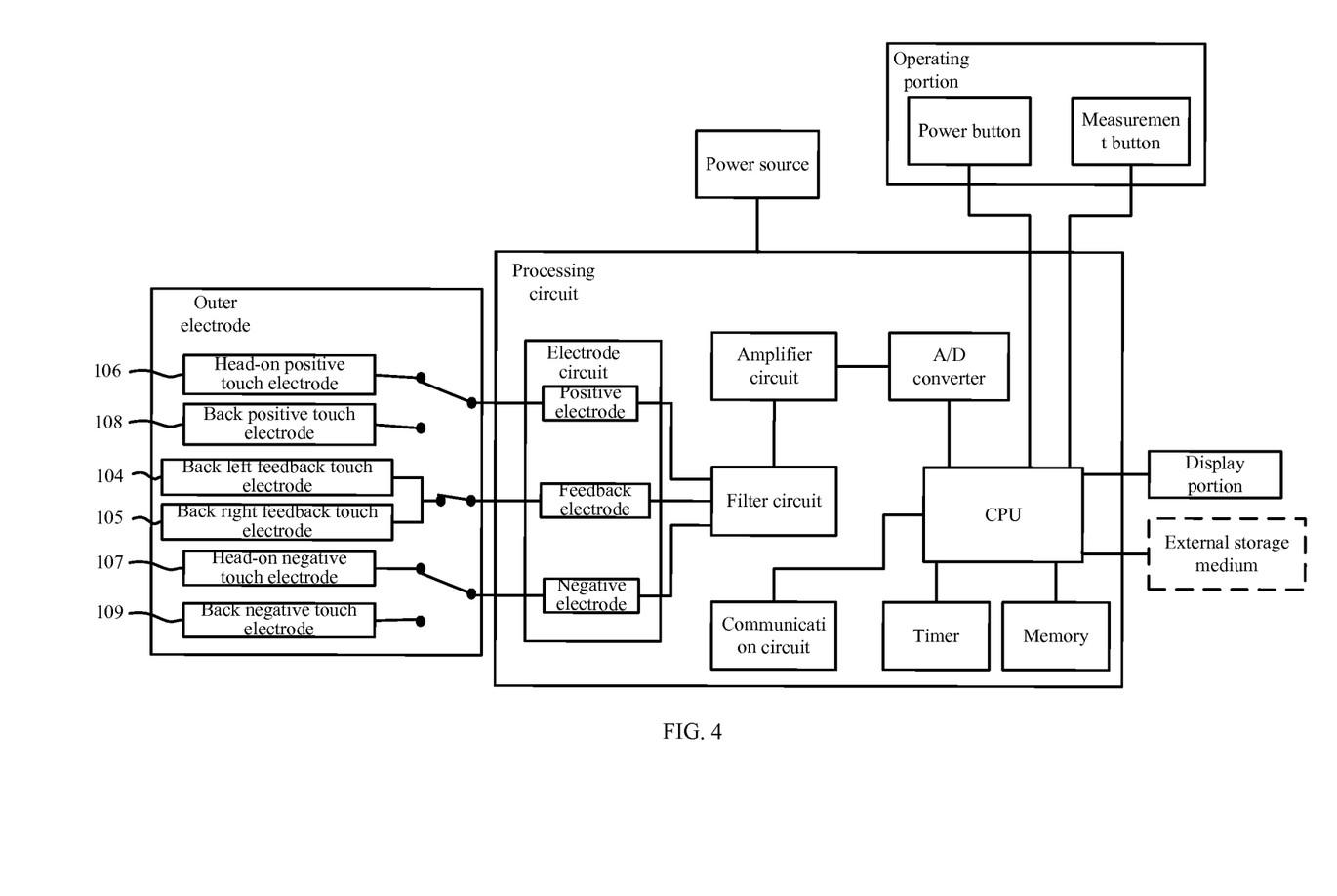
FIG. 4 is a structural schematic diagram of a functional module of a card type electrocardio measuring device according to the present invention.

FIG. 4 is a structural schematic diagram of a functional module of a card type electrocardio measuring device according to the present invention. As shown in FIG. 4, the card type electrocardio measuring device in this embodiment includes an outer electrode, a processing circuit and an operating portion. With reference to FIG. 1, the outer electrode includes a head-on positive touch electrode 106, a back positive touch electrode 108, a back left feedback touch electrode 104, a back right feedback touch electrode 105, a head-on negative touch electrode 107 and a back negative touch electrode 109 in the above embodiment. The operating portion includes a power button and a measurement button for a switch system consisting of the first break-point annular switch 1015, the second break-point annular switch 1016 and elastic switches 1134.

The processing circuit includes: electrode circuit corresponding to the head-on positive touch electrode 106, the back positive touch electrode 108, the back left feedback touch electrode 104, the back right feedback touch electrode 105, the head-on negative touch electrode 107 and the back negative touch electrode 109 described above, where the head-on positive touch electrode 106 and the back positive touch electrode 108 connect to a positive electrode of the electrode circuit, the back left feedback touch electrode 104 and the back right feedback touch electrode 105 connect to a feedback electrode of the electrode circuit, the head-on negative touch electrode 107 and the back negative touch electrode 109 connect to a negative electrode of the electrode circuit, and the electrode circuit is used for detecting an electrical signal of the subject; a filter circuit, connected to the electrode circuit, for filtering out noise from the electrical signal of the subject detected by the electrode circuit; an amplifier circuit, connected to the filter circuit, for amplifying the electrical signal output by the filter circuit, an A/D (Analog/Digital) converter, connected to the amplifier circuit, for converting the amplified electrical signal from an analog signal to a digital signal; a CPU, connected to the A/D converter, for processing and operating a digital signal, receiving various operational button signal instructions issued by the operating portion, performing corresponding process based on the received various operational button signal instructions, and also for writing and reading information to a memory; a memory, connected to the CPU, which can be an ROM (Read Only Memory) or an RAM (Random Access Memory), for storing an algorithm routine to be written and read by the CPU, and database information and etc.; a timer, connected to the CPU, for timing automatically and transmitting timing data to the CPU in real time; and a communication circuit, connected to the CPU, for uploading the measured electrocardio waveforms to an upper computer based on relevant instructions.

Further, since the external electrode includes a plurality of touch electrodes, the card type electrocardio measuring device in this embodiment can have various measurement postures.

Figure 6A:
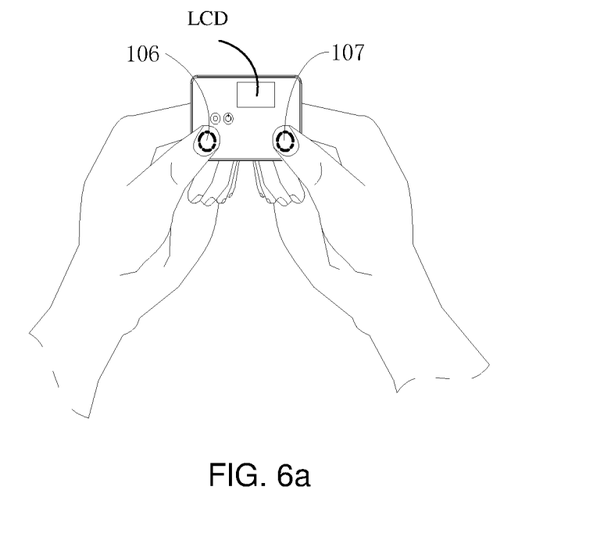
FIG. 6a is a front view of a measuring mode of a card type electrocardio measuring device according to the present invention.
Figure 6B:
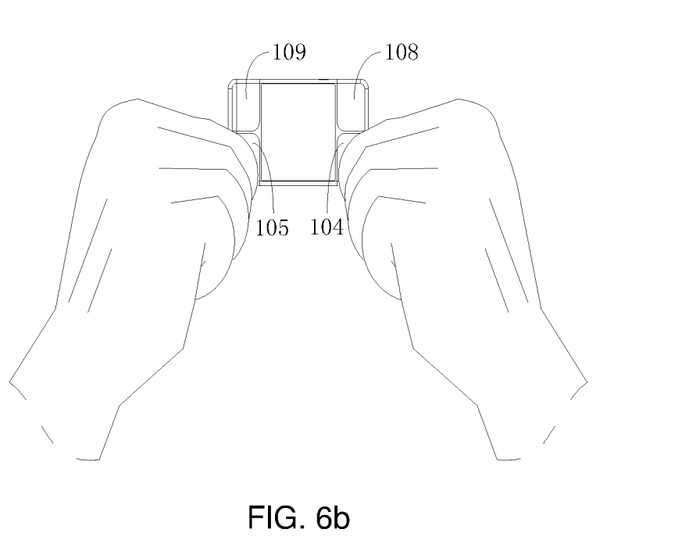
FIG. 6b is a rear view of a measuring mode of a card type electrocardio measuring device according to the present invention.

First, FIG. 6*a* is a front view of a measuring mode of a card type electrocardio measuring device according to the present invention; FIG. 6*b* is a rear view of a measuring mode of a card type electrocardio measuring device according to the present invention, with reference to FIG. 6*a* and FIG. 6*b*, the subject can place his left thumb and right thumb respectively on the head-on positive touch electrode 106 and the head-on negative touch electrode 107, and the left thumb and right thumb are respectively against the back left feedback touch electrode 104 and the back right feedback touch electrode 105, to measure electrocardio waveforms.

Figure 7A:
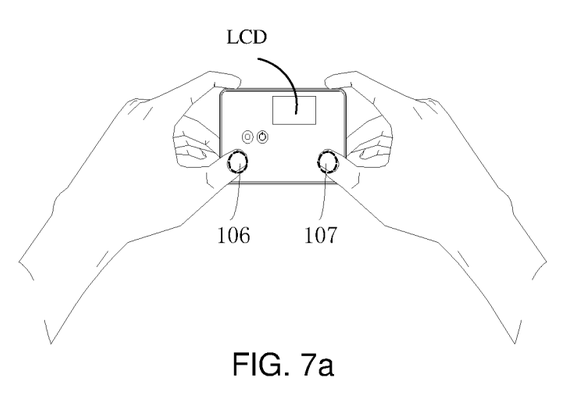
FIG. 7a is a front view of another measuring mode of a card type electrocardio measuring device according to the present invention.
Figure 7B:
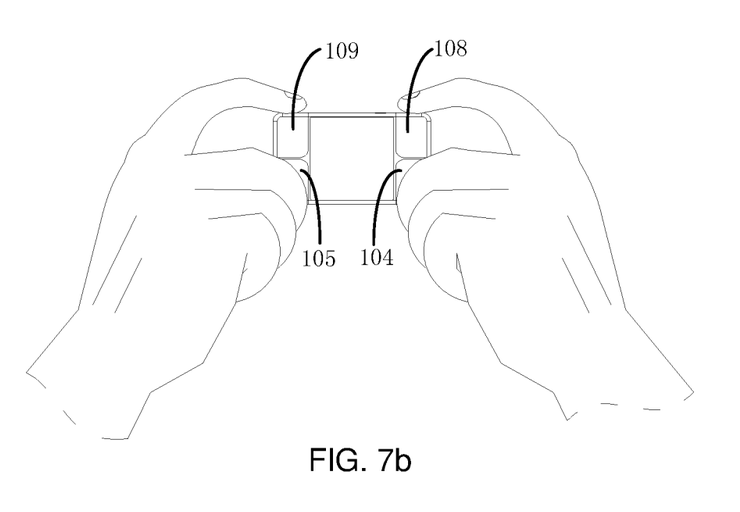
FIG. 7b is a rear view of another measuring mode of a card type electrocardio measuring device according to the present invention.

Second, FIG. 7*a* is a front view of another measuring mode of a card type electrocardio measuring device according to the present invention; FIG. 7*b* is a rear view of another measuring mode of a card type electrocardio measuring device according to the present invention, with reference to FIG. 7*a* and FIG. 7*b*, likewise, the subject can place his left thumb and right thumb respectively on the head-on positive touch electrode 106 and the head-on negative touch electrode 107, but in order to keep the electrocardio measuring device more stably, left middle finger and right middle finger are respectively against the back left feedback touch electrode 104 and the back right feedback touch electrode 105, and the left thumb and right thumb respectively press the edges of the back positive touch electrode 108 and the back negative touch electrode 109.

It can be understood that the handheld measuring postures are not limited to the above two manners, the electrocardio waveforms can be measured when the following conditions are fulfilled: fingers of the left hand touch one of the back left feedback touch electrode 104 and the back right feedback touch electrode 105 on the basis that they touch the head-on positive touch electrode 106 or the back positive touch electrode 108, and fingers of the right hand touch one of the back left feedback touch electrode 104 and the back right feedback touch electrode 105 on the basis that they touch the head-on negative touch electrode 107 or the back negative touch electrode 109.

Figure 8:
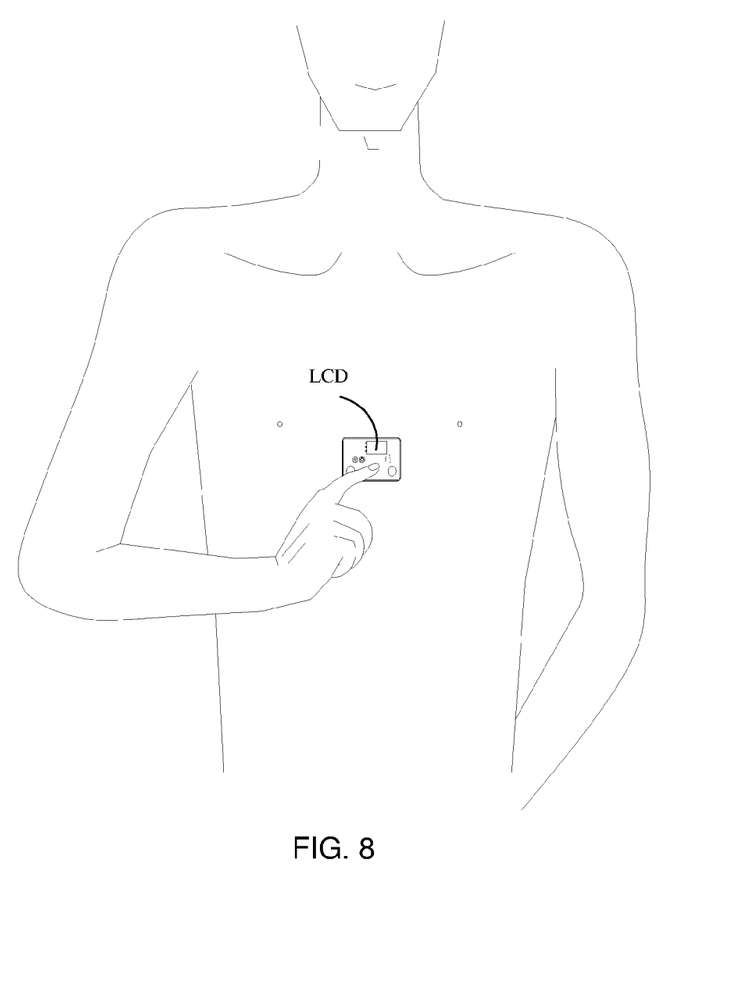
FIG. 8 is a schematic diagram of still another measuring mode of a card type electrocardio measuring device according to the present invention.

Third, FIG. 8 is a schematic diagram of still another measuring mode of a card type electrocardio measuring device according to the present invention, the card type electrocardio measuring device is placed on a user's chest to measure electrocardio waveforms, in particular, the electrocardio waveforms measurement is achieved by contacting the back positive touch electrode 108 and the back left feedback touch electrode 104 simultaneously to the left chest, and contacting the back negative touch electrode 109 and the back right feedback touch electrode 105 simultaneously to the right chest.

Further, since the outer edges and vertex angles of the back touch electrodes in Embodiment 1 are all shaped to be arc chamfers, the measuring posture is suitable for the subject to hold, making the holding experience of the user much better. In particular, for a chest measuring mode, when measuring a man with a robust breast and a woman with a plump breast, the arc chamfers shape of the outer edges and vertex angles of the back touch electrodes are not only makes the subject feel comfortable, but also greatly increases the contact measurement area compared to a dotted-like touch of the existing electrocardio measuring device, therefore, the stability of the electrocardio waveforms measurement can be guaranteed.

It should be emphasized that the card type electrocardio measuring device in this embodiment can achieve I, II, III leads electrocardio waveforms measurement mode for the subject by means of the positive electrode, the negative electrode and the feedback electrode in the electrode circuit, since one hand of the subject should simultaneously touch the positive electrode and the feedback electrode, the other hand should simultaneously touch the negative electrode and the feedback electrode, the intervention of the feedback electrode can help the positive electrode and the negative electrode to filter out a noise signal into a front end of the filter circuit, thereby improving accuracy of measuring electrocardio waveforms.

Further, the card type electrocardio measuring device in this embodiment also includes a display portion, an external storage medium and a power source. The power source is connected to electronic components to be powered, and for powering the card type electrocardio measuring device. Besides, the external storage medium connects with the CPU after being inserted into a socket for placing the external storage medium, and can be used to store the measured electrocardio waveform temporarily. The display portion is connected to the CPU, and under the control of the CPU, and can be used to display data output by the CPU.

Since the external electrode includes a plurality of touch electrodes, the card type electrocardio measuring device in this embodiment can achieve multiple measuring postures, enable the user to change measuring postures freely based on the actual situations when he/she suffers from a self-conscious symptom, such as palpitations or ecphysesis, which needs to perform electrocardio measurement.

Embodiment 3

Figure 5:
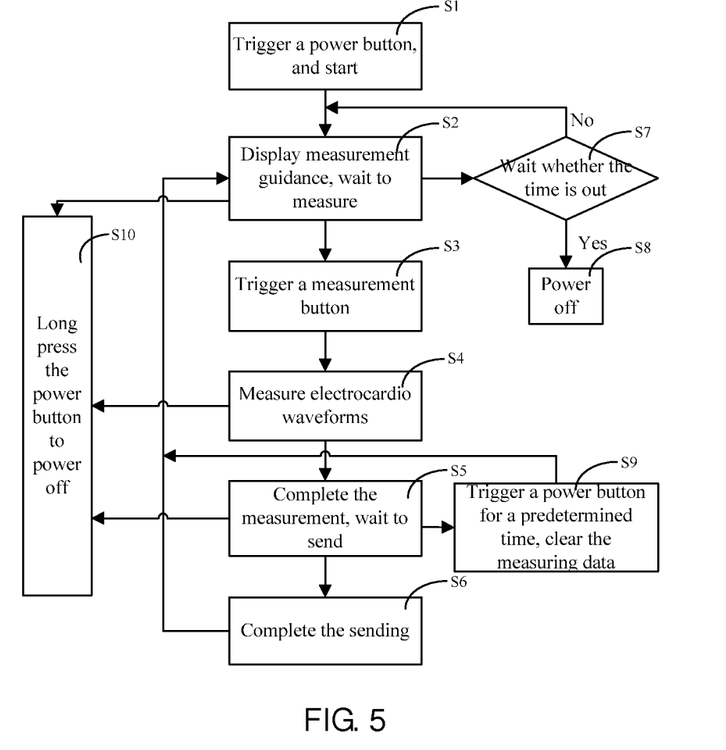
FIG. 5 is a program execution flowchart of a card type electrocardio measuring device according to the present invention.

FIG. 5 is a program execution flowchart of a card type electrocardio measuring device according to the present invention. With reference to FIG. 4 and FIG. 5, the card type electrocardio measuring device according to the present invention has program steps to be executed as follows:

Step S1, Trigger a power button, and start;

In particular, the subject holds in hand the card type electrocardio measuring device, triggers the power button to power on, and program execution begins;

Step S2, Display measurement guidance, wait to measure;

In particular, the display portion displays it is waiting to measure, and displays available measuring posture information for guiding the subject;

Step S3, Trigger a measurement button;

In particular, the subject triggers the measurement button to start the measurement, after an appropriate measuring posture is selected;

Step S4, Measure electrocardio waveforms;

In particular, the display portion displays measurement of the electrocardio waveforms being performed by the device in a manner of counting down the seconds, to prompt the subject to keep the current measuring posture, with the series of operations, for example, the CPU receives operational button signal instructions issued by the operating portion, the electrode circuit detects an electrical signal of the subject, the filter circuit filters out noise from the electrical signal of the subject detected by the electrode circuit, the amplifier circuit amplifies the electrical signal output by the filter circuit, the A/D converter converts the amplified electrical signal from an analog signal to a digital signal, the CPU processes and operates a digital signal, and writes and reads information to a memory, the electrocardio waveforms can be finally measured; the measured electrocardio waveforms can be stored in the memory temporarily;

Step S5, Complete the measurement, wait to send;

In particular, after counting down the seconds is completed, the display portion displays an indication that measurement of the electrocardio waveforms is completed, to prompt the subject to keep relax and thereby release the measuring posture, and wait to respond a reading instruction of the upper computer to send electrocardio waveforms to the upper computer;

Step S6, Complete the sending;

In particular, the reading instruction of the upper computer is received, a channel with the upper computer is established, the electrocardio waveforms stored temporarily in the memory is read, and thus sending to the upper computer is completed;

Step S7, Whether the waiting is overtime;

In particular, when displaying measurement guidance and waiting to measure in step S2, in order to save power of the power source, judge whether the waiting to measure is overtime, if it is overtime, perform step S8, otherwise, continue to perform step S2, to wait to measure;

Step S8, Power off;

Step S9, Trigger a power button for a predetermined time, clear this measuring data;

In particular, after completing the measurement of electrocardio waveforms in step 5, during the waiting to send, if the subject considers the measuring posture adopted in the measurement is not correct, or the measurement is interfered by the surrounding environment, or the measurement is not performed in a relative calm state, then triggers the power button for a predetermined time, such as 3 seconds by long press, to clear the measuring data, and thereby jumps to perform step S2;

Step S10, Long press the power button to power off.

In particular, when displaying measurement guidance and waiting to measure in step S2, measuring electrocardio waveforms in step S4, and completing the measurement, waiting to send in step S5, if long press the power button, such as for 5 seconds, it can be powered off directly.

The program execution flow of the card type electrocardio measuring device has been described in detail in this embodiment, due to the adoption of relevant technical solutions that: after completing the measurement of electrocardio waveforms, waiting to send the electrocardio waveforms, the subject can autonomously select to clear the measuring data based on the actual situations, so that processing authority of the subject to timely complete the electrocardio waveforms can be added, the subject can autonomously and quickly select more effective electrocardio waveforms to store, and provide reliable measuring data to the subsequent effective electrocardio analysis.

It should be understood that, terms used for describing the present invention, such as "central", "upper", "lower", "front", "rear", "left", "right", "vertical", "horizontal", "top", "bottom", "inner" and "outer" show orientation or position relationship based on the accompanying drawings, are only used to simplify description of the present invention, and not to indicate or imply that the device or element referred to must have a particular orientation, or be configured and operated in a particular orientation, thus they can not be construed as limiting the present invention. When describing the present invention, unless otherwise indicated, term "plurality" is defined as two or more than two.

It should be understood that, terms used for describing the present invention, such as "mounted", "joined", "connected" should be broadly interpreted, unless otherwise indicated, for example, it can be removably connected, or fixedly connected, or integrally connected; and it can be connected directly or through an intermediate therebetween or communicated internally between two elements. Persons skilled in the art can understand specific meanings of the above terms in the present invention depending on specific application.

Reference throughout this specification to "one embodiment", "some embodiments", "exemplary embodiment", "example", "specific example", or "some examples" means that a particular feature, structure, material or characteristic described in connection with the embodiment or exemplary description is included in at least one embodiment or example of the present invention. Illustrative expressions of the above terms throughout this specification do not necessarily all refer to the same embodiment or example. Moreover, the particular feature, structure, material or characteristic may be combined in any suitable manner in one or more embodiments or examples.

While embodiments have been shown and described, it will be understood by persons skilled in the art that various alterations, modifications, replacements or variations may be made to these embodiments without departing from the spirit and principle of the present invention, and the scope of the present invention should be limited by the appended claims and their equivalents.

What is claimed is:

1. A card type electrocardio measuring device, comprising:
    a main body bracket, with a hollow shape;
    a back encapsulation, arranged on a back of the main body bracket, wherein the back encapsulation comprises:
    a back bracket; and
    four back touch electrodes, arranged around the back bracket; and
    a circuit board, arranged on a front of the main body bracket, wherein electronic components on the circuit board are respectively accommodated fitly between a back of the circuit board and the back encapsulation, in a way of penetrating a hollow portion of the main body bracket.

2. The card type electrocardio measuring device according to claim 1, wherein the electronic components are all arranged on the back of the circuit board, and a front of the circuit board and a front frame of the main body bracket are in a same horizontal plane.

3. The card type electrocardio measuring device according to claim 1, wherein outer edges of each of the back touch electrodes and a vertex angle formed by the outer edges of each of the back touch electrodes are shaped to be arc chamfers.

4. The card type electrocardio measuring device according to claim 1, wherein the back bracket comprises:
    a sheet-shaped body;
    a plurality of projections, respectively perpendicular to the sheet-shaped body, wherein the main body bracket is correspondingly provided with blind holes for engaging the plurality of projections, the back bracket is snapped into the back of the main body bracket, and the back bracket and the main body bracket are connected by respectively embedding the plurality of projections into the blind holes.

5. The card type electrocardio measuring device according to claim 4, wherein the back bracket is made of metallic materials, and the back bracket and the main body bracket are integrally molded.

6. The card type electrocardio measuring device according to claim 1, wherein the back touch electrode comprises:
    a vertical welding portion, wherein the main body bracket is correspondingly provided with through-holes for engaging the vertical welding portion;
    a horizontal engaging portion, embedded into both edges of the back bracket's exterior corner, wherein the vertical welding portion passes through the through-hole to weld with the circuit board.

7. The card type electrocardio measuring device according to claim 6, wherein a top of a portion where the vertical welding portion passes through the through-hole, the vertical welding portion and a front frame of the main body bracket are in a same horizontal plane.

8. The card type electrocardio measuring device according to claim 6, wherein the circuit board comprises:
    a filter circuit; and
    an electrode circuit, wherein the electrode circuit includes:
    a positive electrode, connected with the filter circuit;
    a negative electrode, connected with the filter circuit, wherein the positive electrode and the negative electrode are used to introduce body potential change of a subject to the filter circuit;
    a feedback electrode, connected with the filter circuit, wherein the feedback electrode is used to help the positive electrode and the negative electrode to filter out a noise signal into a front end of the filter circuit, the four back touch electrodes comprise:
    a back left feedback touch electrode, arranged at a left lower corner of the back of the main body bracket and connected with the feedback electrode;
    a back right feedback touch electrode, arranged at a right lower corner of the back of the main body bracket and connected with the feedback electrode;
    a back positive touch electrode, arranged at a left upper corner of the back of the main body bracket and connected with the positive electrode;
    a back negative touch electrode, arranged at a right upper corner of the back of the main body bracket and connected with the negative electrode.

9. The card type electrocardio measuring device according to claim 8, further comprising: a strip-shaped battery, wherein the circuit board is provided with a battery hollow portion for accommodating fitly the strip-shaped battery, the strip-shaped battery is arranged within the battery hollow portion along its long edge, with one side of the strip-shaped battery being against the back encapsulation, and the other side of the strip-shaped battery and a front of the circuit board being in a same horizontal plane.

10. The card type electrocardio measuring device according to claim 9, further comprising:
    a head-on positive touch electrode, arranged on the front of the circuit board and at one side of the battery hollow portion, and connected with the positive electrode;
    a head-on negative touch electrode, arranged on the front of the circuit board and at the other side of the battery hollow portion, and connected with the negative electrode.

11. The card type electrocardio measuring device according to claim 2, further comprising:
- a buzzer, wherein the main body bracket is provided with a buzzer slot for accommodating fitly the buzzer, and the buzzer is provided within the buzzer slot;
- an LCD, wherein the main body bracket is provided with an LCD slot for engaging the LCD, the circuit board is provided with an LCD hollow portion for accommodating fitly the LCD, the LCD slot is located above the buzzer slot, and the LCD engages the LCD slot via the LCD hollow portion and is supported by the buzzer slot.

12. The card type electrocardio measuring device according to claim 11, wherein an LCD panel of the LCD engaged the LCD slot and the front of the circuit board are in the same horizontal plane.

13. The card type electrocardio measuring device according to claim 11, wherein the buzzer slot is of a split structure, and a gap of the split structure is for accommodating fitly a line connecting the buzzer and the circuit board.

14. The card type electrocardio measuring device according to claim 10, further comprising: a strong seal for sealing the front of the circuit board, on which it is provided with an electrode through-hole for revealing the head-on positive touch electrode and the head-on negative touch electrode.

15. The card type electrocardio measuring device according to claim 11, further comprising: a strong seal, for sealing the front of the circuit board, and provided with a window for transparently sealing the LCD.

16. The card type electrocardio measuring device according to claim 1, wherein the circuit board is printed with a first break-point annular switch for switching a power source and a second break-point annular switch for activating measurement, each of the first break-point annular switch and the second break-point annular switch comprises an annular electrode and a circular electrode, which are arranged concentrically and insulated from each other through a circular groove.

17. The card type electrocardio measuring device according to claim 16, further comprising: a strong seal for sealing a front of the circuit board, which is provided with elastic switches respectively corresponding to the first break-point annular switch and the second break-point annular switch for turning on the first break-point annular switch and the second break-point annular switch.

18. The card type electrocardio measuring device according to claim 17, wherein each of the elastic switches is a raised elastic tongue, wherein the annular electrode is electrically connected to the circular electrode by pressing the elastic tongue to a flattened state.

* * * * *